United States Patent
Gerder-Kallisch et al.

(10) Patent No.: US 11,422,684 B2
(45) Date of Patent: Aug. 23, 2022

(54) INPUT SYSTEM AND PROCESS FOR CONTROLLING AN ELECTROMEDICAL DEVICE

(71) Applicant: Drägerwerk AG & Co. KGaA, Lübeck (DE)

(72) Inventors: Ulrike Gerder-Kallisch, Lübeck (DE); Andreas Neumann, Klempau (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 40 days.

(21) Appl. No.: 17/257,064

(22) PCT Filed: Jun. 12, 2019

(86) PCT No.: PCT/EP2019/065265
§ 371 (c)(1),
(2) Date: Dec. 30, 2020

(87) PCT Pub. No.: WO2020/007577
PCT Pub. Date: Jan. 9, 2020

(65) Prior Publication Data
US 2021/0157463 A1 May 27, 2021

(30) Foreign Application Priority Data
Jul. 2, 2018 (DE) .......................... 102018005193.6

(51) Int. Cl.
*G06F 3/0484* (2022.01)
*G16H 40/67* (2018.01)
(Continued)

(52) U.S. Cl.
CPC ........... *G06F 3/0484* (2013.01); *G16H 40/40* (2018.01); *G16H 40/67* (2018.01); *G06F 9/445* (2013.01)

(58) Field of Classification Search
CPC ...................................................... G06F 3/0484
(Continued)

(56) References Cited

U.S. PATENT DOCUMENTS

2006/0059412 A1* 3/2006 Lefebvre ............... G06F 40/117
715/256
2008/0312512 A1* 12/2008 Brukalo ................. G16H 20/17
600/300
(Continued)

FOREIGN PATENT DOCUMENTS

DE 102012003509 A1 8/2013
DE 102015112796 A1 3/2016

OTHER PUBLICATIONS

Penta GmbH: Medizinische PC's und Monitore für OP, Intensiv, Radiologie, Chirurgie, Endoskopie und Mobile Anwendungen.

*Primary Examiner* — Reza Nabi
(74) *Attorney, Agent, or Firm* — McGlew and Tuttle, P.C.

(57) ABSTRACT

A process for the operation of a type A medical device (10) together with a type B medical device (12) includes connecting the medical devices (10, 12) communicatively to one another. The type A medical device (10) includes a display device (14) suitable for the display of texts in different languages. The type B medical device (12) has no text display features. The type B medical device (12) transmits a datagram (22) with an information identifier (44) to the type A medical device (10) for displaying a textual or at least partially textual piece of information (20). Upon receipt of an information identifier (44) from a medical device database (26), the type A medical device (10) loads a piece of information (20) consistent with the information identifier (44) and displays this piece of information with the display device (14) and for the type B medical device (12).

10 Claims, 3 Drawing Sheets

(51) Int. Cl.
  *G16H 40/40* (2018.01)
  *G06F 9/445* (2018.01)
(58) Field of Classification Search
  USPC .......................................................... 715/703
  See application file for complete search history.

(56) References Cited

U.S. PATENT DOCUMENTS

| | | | | |
|---|---|---|---|---|
| 2008/0312584 A1* | 12/2008 | Montgomery | ......... | G16H 40/67 600/300 |
| 2008/0312585 A1* | 12/2008 | Brukalo | ................ | G08C 17/00 604/67 |
| 2009/0112626 A1* | 4/2009 | Talbot | .................... | G16H 40/67 600/300 |
| 2010/0115052 A1* | 5/2010 | Ishii | ........................ | G09B 5/00 709/217 |
| 2013/0084905 A1* | 4/2013 | Ehara | ..................... | H04W 4/70 455/500 |
| 2013/0213399 A1* | 8/2013 | Hansmann | .......... | A61M 16/024 128/204.23 |
| 2014/0113553 A1* | 4/2014 | Brukalo | ................ | G16H 20/17 455/41.1 |
| 2014/0215330 A1* | 7/2014 | Lee | ..................... | G06F 3/04847 715/703 |
| 2015/0004575 A1* | 1/2015 | Rath | ..................... | G16H 20/30 434/236 |
| 2015/0347701 A1* | 12/2015 | Atkin | .................... | G16H 40/67 705/2 |
| 2016/0027399 A1* | 1/2016 | Wilde | ................. | H04L 65/1083 345/520 |
| 2016/0033308 A1* | 2/2016 | Wiessflecker | ........... | H04W 4/70 702/127 |
| 2016/0051146 A1* | 2/2016 | Eaton | .................. | A61B 5/0205 340/870.07 |
| 2016/0202906 A1* | 7/2016 | Abuelsaad | ........... | G06F 40/174 715/746 |
| 2016/0378305 A1* | 12/2016 | Shibukawa | ............ | G06F 3/1205 715/703 |
| 2019/0102076 A1* | 4/2019 | Naidoo | ................ | G06F 40/166 |
| 2020/0261644 A1* | 8/2020 | Farnan | .............. | A61M 5/14248 |

\* cited by examiner

INPUT SYSTEM AND PROCESS FOR CONTROLLING AN ELECTROMEDICAL DEVICE

CROSS REFERENCE TO RELATED APPLICATIONS

This application is a United States National Phase Application of International Application PCT/EP2019/065265, filed Jun. 12, 2019, and claims the benefit of priority under 35 U.S.C. § 119 of German Application 10 2018 005 193.6, filed Jul. 2, 2018, the entire contents of which are incorporated herein by reference.

TECHNICAL FIELD

The present invention pertains to a process for the operation of a medical device, namely a process for outputting messages, alarms, status information, operating instructions or a part of the operating instructions and the like, each in text form or at least also in text form—designated in summary as information below—by means of a medical device, which itself has no text display option, and to a medical device operating according to the process.

TECHNICAL BACKGROUND

In situations, in which an output of a piece of information of the above-mentioned type would be meaningful and can be expected in the future by the user and the operator, medical devices without their own text display option cannot display the piece of information.

Typical devices of this type are "simple" medical devices, which are limited in terms of text output options, namely especially measuring devices or medical devices with electronic (sequence) control, for example, infusion pumps, feeding pumps, blood pressure measuring devices, and to some extent also $SPO_2$ measuring devices as well as $CO_2$ monitors in a simple configuration.

Such medical devices without a display or with only a one-to-three line alphanumerical display, for example, with a display in the form of an LCD display or LED display, can only output a short text or an error code in a manner like, for example, "F17" in addition to acoustic alarm messages (horn) as visual alarm messages (for example, by means of a status LED). A user of the medical device must then "translate" these alarm messages by means of operating instructions.

To obtain a text output option also for such medical devices, it was and is often a possible solution to replace a hitherto alphanumerical display with a graphic (color) display in the next generation of devices. Text outputs in non-Latin alphabets are possible by means of such a display as well. In general, features, for example, an online help and/or a context-sensitive help can be achieved in the first place with a display with a text output option.

The drawbacks of such an addition of a text output option to "simple" medical devices are obvious because at least there are higher costs. However, these drawbacks apparently cannot be avoided because a medical device, which outputs information in text form or at least also in text form, must basically be able to be used in different countries, so that the respective information must be able to be outputted in different languages. Thus, the IEC 60601-1, 3rd edition stipulates as applicable and European harmonized standard that safety information on a medical device must be made available in the corresponding national language. The EU Regulation 2017/745 of Apr. 5, 2017—Medical Device Regulation (MDR) stipulates in Article 7 that labels on a medical device or descriptions for the medical device may not be ambiguous for a user or patient. The resulting need for outputting a respective piece of information in different languages leads to a corresponding complexity in the implementation of the text output option. In this case, especially when languages with a non-Latin alphabet shall also be supported, this further increases the complexity. In addition, all supported languages must be taken into account in later adaptations, additions to or changes in the information to be outputted in text form.

SUMMARY

One object of the present invention is to provide a process for the operation of a medical device and a medical device operating according to the process, in which the above-mentioned drawbacks are avoided or at least the consequences thereof are reduced.

This object is accomplished according to the present invention by means of a process for operation of a medical device, namely by means of a process for the operation of the medical device (first medical device, type A medical device, medical device of a first type) together with at least one other medical device (second medical device, type B medical device, medical device of a second type) with the features of the invention.

For this purpose, for the operation of a first medical device (type A medical device) together with at least one second medical device (type B medical device), provisions are made for the at least two medical devices to be connected communicatively to one another, for the first medical device to comprise a display device suitable for the display of texts, especially of texts in different languages and/or in different alphabets (different characters), and for the second medical device to have no text display option of its own, i.e., especially to have no display device like the first medical device.

The first medical device and the at least one second medical device thus possibly differ with regard to their function, for example, because the first medical device functions as a ventilator and the second medical device functions as a syringe pump. The medical devices differ, however, at least by one of the two medical devices comprising a display device of the above-mentioned type and the other medical device not comprising such a display device.

Correspondingly, in the sense of the present invention, the medical devices are also called type A medical device and type B medical device below for distinction, wherein a type A medical device is a medical device with such a display device and a type B medical device is a medical device without such a display device. So that a display of a textual piece of information is also possible for a type B medical device, the type A medical device "allows" the type B medical device a "shared use" of its own display device to some extent. A piece of information that is displayed by the type A medical device for the type B medical device is displayed as guest display or daughter display by means of the display device of the type A medical device. For this, the second medical device (the type B medical device) transmits a datagram with an information identifier to the first medical device (to the type A medical device) for displaying a textual or at least partially textual piece of information. Upon receipt of such an information identifier, the first medical device loads (receives) from a medical device database a piece of information consistent with the information identifier and displays this piece of information (information) by means of its own display device. The medical device database is preferably a database stored in a memory of the first medical device. As an alternative, the medical device database or a part of the medical device database may also be stored in a memory which is remote and available communicatively for the first medical device, for example, on a hospital server or the so-called cloud.

DE 10 2012 003 509 A1 and DE 10 2015 112 796 A1 were determined to be the state of the art in a patent office search for priority-establishing applications underlying the present application. These patents show each a device without its own text display option in the sense of the present invention, i.e., a type B device in the sense of the above terminology. These devices record data during the operation and make use of a display option of another, remote device (type A device) for the display of the recorded data, wherein the two devices are connected communicatively for data transmission. However, only the data to be displayed are each transmitted to the remote type A device and only the display of the data recorded by the type B device, i.e., a display of recorded measured values is carried out there. However, data to be displayed are not transmitted to the type A medical device in the process of the invention. Rather, an information identifier is instead transmitted from the type B medical device to the type A medical device, which codes the information to be displayed. The transmitted information identifier itself is not displayed now, unlike the datum transmitted there in case of the state of the art. The use of an information identifier for coding the information to be displayed makes it possible, for example, to display the information to be displayed on the type A medical device in a corresponding national language, especially in a national language set at the type A medical device. A consideration of such settings or similar settings is not possible in case of a direct display of a respectively transmitted datum.

The process being proposed here and embodiments of the process described below and the process steps comprised by it are carried out automatically, i.e., without a special intervention of the user of the respective medical device. The automatic carrying out of the process steps takes place under the control of a control unit of the respective medical device. These control units comprise a processing unit each in the form of or like a microprocessor as well as a memory. A control program that can be executed by the processing unit and is executed during the operation of a respective medical device by the processing unit thereof, is loaded or can be loaded in the memory. In this respect, the above-mentioned object is also accomplished by means of a control unit intended for the control of a medical device, which control unit operates according to the process as described here and below and for this purpose comprises means for carrying out the process (the processor with loaded software is configured to carry out the process).

The present invention is preferably implemented with software running on one or more processor (computer). The present invention is thus, on the one hand, also a computer implemented process—program code instructions, which can be executed by a computer and with storage medium with such a computer program, i.e., a computer program product with program code means, as well as finally also a control unit or a medical device with memory, which control unit/medical device with loaded computer program carries out the process and its configurations.

One advantage of the present invention is that in the configuration without its own display option, the type B medical device may continue to be a "simple" medical device, and no upgrading of such a medical device in the sense of an addition of its own, possibly high-quality graphic display option is necessary. Another advantage is also a now possible central alarm generation of a plurality of, many or all alarm generation sources of a patient directly at only one output point. Each type B medical device is basically an alarm generation source and an alarm situation may arise with regard to each alarm generation source when using a plurality of alarm generation sources in the treatment of a patient. By a display of alarms or the like of such type B medical devices being carried out by means of a display device of a type A medical device communicatively available for these medical devices, namely a medical device, which has its own display option, the type A medical device functions as a central output point of many or all alarm generation sources and medical staff must only still or primarily monitor the display device of this type A medical device.

References used here indicate the further configuration of the subject of the principal claim by means of the features of the respective subclavia and shall not be considered to represent an abandonment of the wish to achieve an independent, concrete protection for combinations of features of the dependent claims. Furthermore, it shall be assumed in respect to an interpretation of the claims as well as of the description in case of a more specific concretization of a feature in a dependent claim that such a limitation is not present in the respective, preceding claims as well as in a more general embodiment of the concrete process or medical device. Any reference in the description to aspects of dependent claims shall accordingly also expressly imply a description of optional features even without special reference. Finally, it should be pointed out that the process proposed here may also be perfected corresponding to the dependent device claims and vice versa.

In one embodiment of the process, a language can be selected for the type A medical device and an identifier of a selected language is stored in a memory of the type A medical device in the form of a datum called country setting below. By means of the country setting, in which country the type A medical device is being operated can be defined, and/or a national language can be selected. Upon receipt of an information identifier from the type B medical device or from a type B medical device, the type A medical device then loads from the medical device database not only a piece of information consistent with the information identifier, but a piece of information consistent both with the information identifier and with the country setting. This piece of information (information) is then displayed by means of the display device of the type A medical device. By the type A medical device also taking into consideration the country setting, the information to be displayed from the medical device database is loaded in a corresponding national language. A country setting is a setting, which is normally provided anyway for the type A medical device. By the type A medical device taking into consideration the country setting also in connection with a display of a piece of information for the type B medical device or for a type B medical device, any guest information is also automatically displayed in the correct language as well as possibly in an alphabet necessary for the display of the corresponding language.

In another embodiment of the process, the datagram transmitted to the type A medical device from the type B medical device or from a type B medical device identifies the transmitting type B medical device, and upon receipt of an information identifier from the type B medical device, the type A medical device loads a piece of information from the medical device database, which is consistent with the identification of the type B medical device and with the information identifier or with the identification of the type B medical device, with the information identifier and with the country setting. In this case, the datagram identifies the transmitting type B medical device, for example, by this type B medical device comprising a device identifier as part of the user data or by this type B medical device comprising a transmitter identifier according to the protocol valid for the sending thereof. Taking at least the information identifier and the identification of the type B medical device simultaneously into consideration during the loading of a piece of information from the medical device database makes it possible to use "short" information identifiers because each piece of information to be displayed is clearly defined together with the identification of the type B medical device, even if a different type B medical device of a different device category could basically transmit the same information identifier.

In a preferred embodiment of the process, the type A medical device takes into account a priority connected with the information in case of a display of a piece of information for the type B medical device for a type B medical device, wherein the priority arises on the basis of the information, the underlying information identifier, the type B medical device transmitting the information identifier and/or a type or a device category of the type B medical device transmitting the information identifier. Taking priorities into account in this manner allows a higher-priority automatic display of an especially important piece of information for a type B medical device. The taking of priorities into account is especially relevant if a plurality of datagrams each with an information identifier are received in the type A medical device at the same time or essentially at the same time, and all pieces of information specified thereby cannot be displayed at the same time or also shall not be displayed at the same time in the particular case. Each priority taken into account here may arise based on the information loaded from the medical device database or the underlying information identifier. For example, a numerical information identifier, on the one hand, may precisely code in the medical device database a piece of information which can be polled from it database and at the same time code a priority (higher numerical value of the information identifier=higher priority). In addition or as an alternative, a priority automatically taken into consideration by the type A medical device in case of a display of a piece of information for a type B medical device may also arise based on the type B medical device or based on a device category of the type B medical device, so that, for example, a medical device in the form of a feeding pump receives a lower priority compared to a medical device in the form of a blood pressure measuring device.

When taking priorities into account, provisions are optionally made for a first piece of information—a piece of information to be displayed for a first type B medical device—and for a second piece of information—a piece of information to be displayed for a second type B medical device—with identical priorities to be displayed in an alternating manner, at least partly overlapping one another and partly transparently and/or in non-overlapping areas of the display device of the type A medical device. This represents a simple and efficient possibility to display pieces of information with identical priority simultaneously or quasi simultaneously.

In an alternative embodiment of a process for the operation of a type A medical device and of at least one type B medical device or even in case of a special embodiment of one of the variants of the process described above, the information to be displayed for the type B medical device is independent of an exceptional situation or the like on the part of the type B medical device. Rather, such a process allows a display of operating instructions of the type B medical device by means of the display device of the type B medical device. As this was already described above, a language is selected for the type A medical device and an identifier of a selected language is stored as country setting in a memory of the type A medical device in the process. The datagram transmitted to the type A medical device from the type B medical device identifies the transmitting type B medical device, and based on the identification of the type B medical device and on the country setting, operating instructions for the type B medical device are loaded from the medical device database or from another database available for the type A medical device on the part of the type A medical device and by the type A medical device and are displayed as information by means of the display device of the type A medical device. Such a datagram, which subsequently leads to a display of the operating instructions of the transmitting type B medical device by means of the display device of the type A medical device (in the corresponding national language), is, for example, automatically transmitted by the type B medical device when an operating action is taken at the type B medical device, for example, in the form of an actuation of a button at the type B medical device, which is intended to trigger a display of the operating instructions.

In a special embodiment of a process of the type outlined above, i.e., of a process, in which the type A medical device displays the operating instructions for a type B medical device in the language set at the respective type A medical device, a concrete section of the operating instructions for the type B medical device is loaded and displayed by means of the display device on the part of the type A medical device and by the type A medical device with additional consideration of an information identifier comprised by the datagram. The operating instructions of the type B medical device are then displayed by the type A medical device in the manner of a so-called "context-sensitive" help, wherein the information identifier comprised by the datagram defines the particular context.

For carrying out the process as described here and below or for carrying out individual variants of the process, a computer program functioning as a control program for the respective medical device is provided for the type A medical device and for each type B medical device communicatively connected to it. The control program of the respective medical device comprises an implementation of the part of the process that is relevant for the respective medical device, i.e., program code means in order to execute all process steps on the type A medical device and on the type B medical device.

The above-mentioned object is also accomplished by means of a type A medical device and a type B medical device, which are each intended and suitable for carrying out the concrete process or individual embodiments thereof. A corresponding type A medical device also comprises a display device suitable for the display of texts in different languages and/or in different alphabets and/or characters as well as a processing unit in the form of one or more microprocessors as well as memory, wherein a control program of the above-mentioned type is loaded in the memory of the type A medical device, which control program is executed by means of the processing unit of the type A medical device during the operation of the type A medical device. A corresponding type B medical device also comprises a processing unit in the form of one or more microprocessors as well as memory, but does not include a display device suitable for the display of texts at least also in different languages and/or in different alphabets (different characters), wherein a control program of the above-mentioned type is loaded in the memory of the type B medical device, which control program is executed by means of the processing unit of the type B medical device during the operation of the type B medical device.

The above-mentioned object is finally also accomplished by means of a system comprising a type A medical device as well as at least one type B medical device of the above-mentioned type, wherein the at least two medical devices are connected communicatively to one another, wherein a datagram with an information identifier can be transmitted to the type A medical device by the type B medical device or by a type B medical device for displaying a textual or at least partially textual piece of information and is transmitted during operation of the system, and wherein a piece of information consistent with the information identifier can be loaded by means of the type A medical device upon receipt of an information identifier from the type B medical device or from a type B medical device from a medical device database and this piece of information can be displayed by means of the display device and is loaded during operation of the system from the medical device database and is displayed by means of the display device.

An exemplary embodiment of the present invention is explained in more detail below on the basis of the drawings. Objects or components corresponding to one another are provided with the same reference numbers in all figures.

The exemplary embodiment or each exemplary embodiment shall not be considered to represent a limitation of the present invention. Rather, variations and modifications, especially such variants and combinations which the person skilled in the art can find in respect to accomplishing the object, for example, by a combination or variation of individual features described in connection with the general or special part of the description as well as contained in the claims and/or in the drawings and lead to a new subject by combinable features, are possible within the framework of the present disclosure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing two medical devices, one of which has a display device for displaying alarm or error messages and the like;

DESCRIPTION OF PREFERRED EMBODIMENTS

Figure 1:
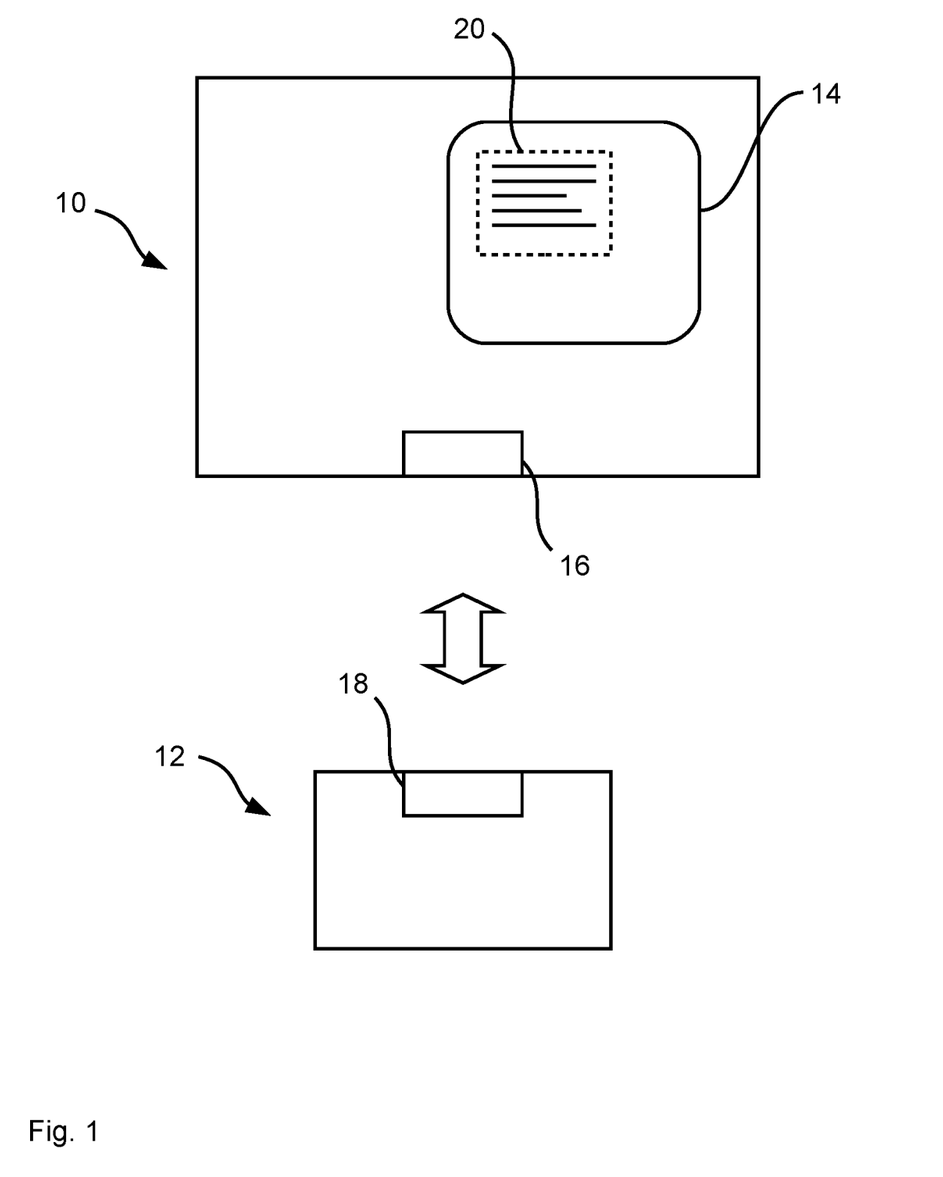

Referring to the drawings, the view according to FIG. 1 shows a first medical device 10 and a second medical device 12 in a schematically simplified general view. The two medical devices 10, 12 differ from each other by a particular function, but especially also by one of the medical devices 10, 12, the first medical device 10 here, having a display device 14 with a text output option in the form of or like a monitor, while the other medical device 10, 12, the second medical device 12 here, has no such display device 14 or at least no display device 14 with comparable display options. The second medical device 12 may have, for example, a simple display or status displays or the like. Such a simple display is not considered to be a display device 14 in the sense of the present invention.

The two medical devices 10, 12 are set up for a data exchange with one another and for this purpose have a communication interface 16, 18 each in a manner basically known per se. The exchange of data is illustrated in the view according to FIG. 1 by means of the block arrow between the two communication interfaces 16, 18. The exchange of data described below can take place directly from one of the two medical devices 10, 12 to the respective other medical device 10, 12. The two medical devices 10, 12 are then wire or wirelessly connected directly to one another by means of the communication interfaces 16, 18, for example, by means of at least one line allowing data transmission. The exchange of data from one of the medical devices 10, 12 to the respective other medical device 10, 12 may also take place over a network, to which each medical device 10, 12 with its communication interface 16, 18 is connected either directly or indirectly in a manner basically known per se.

As far as the present invention is concerned, the data exchange takes place in order to make possible an output of a textual piece of information 20 or a piece of information 20 at least also comprising text of the type mentioned in the introduction, i.e., especially an output of alarms, status messages and the like, for the medical device 10, 12 without display device 14 by means of the display device 14 of the other medical device 10, 12.

The approach disclosed here comes into consideration for basically any medical devices 10, 12. A medical device 10 with a display device 14 with a text output option or at least also with a text output option is correspondingly called a type A medical device 10 and a medical device 12 without such a display device 14 is called a type B medical device. An example of a type B medical device 12 is a so-called syringe pump. An example of a type A medical device 10 is an anesthesia device or a ventilator.

After establishing a communicative connection between a type B medical device 12 and a type A medical device 10 or after activating both medical devices 10, 12, a test to determine whether the type A medical device can display a piece of information 20 for the type B medical device is first carried out. The thereby resulting exchange of data is shown schematically in the view according to FIG. 2. The type B medical device 12 then transmits a datagram 22 to the type A medical device 10. The datagram 22 comprises as user data a device identifier 24 identifying the type B medical device 12, especially a device identifier 24 identifying a device type of the type B medical device 12. The type A medical device 10 checks the received device identifier 24 based on the contents of a medical device database 26 loaded, for example, in its own memory. This device identifier comprises texts for alarms, error messages, status messages and the like as well as optionally help texts and/or electronic manuals for at least one type B medical device 12 or for at least one device type of a type B medical device 12. The medical device database 26 optionally comprises also texts for alarms, error messages, status messages and the like as well as optionally help texts and/or electronic manuals for the type A medical device 10, in the memory of which the medical device database 26 is loaded. In case of a medical device database 26 not loaded in a local memory of the type A medical device 10 and communicatively available for the type A medical device 10, this medical device database preferably comprises texts for alarms, error messages, status messages and the like as well as optionally help texts and/or electronic manuals for different type A medical devices 10 and type B medical devices 12.

Figure 2:
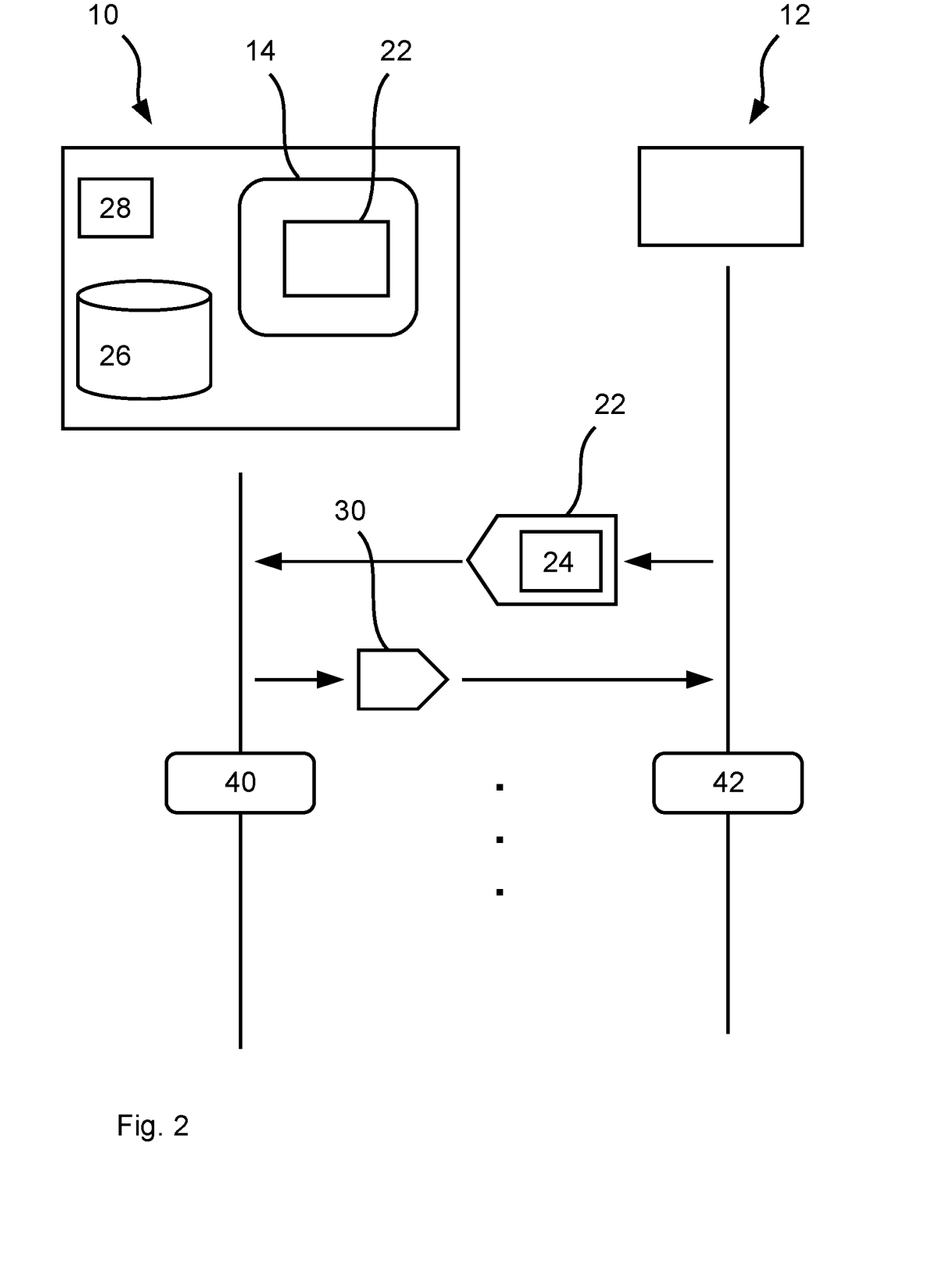
FIG. 2 is a schematic view illustrating a transmission of data between the two medical devices according to FIG. 1 for a first-time establishing a connection ("pairing")

If the medical device database 26 comprises such texts for a type B medical device 12 identified by the received device identifier 24, the basic suitability of the type A medical device 10 is determined for displaying information 20 for the type B medical device 12.

In another, basically optional step, the type A medical device 10 checks whether a display of pieces of information (information) 20 for the type B medical device 12 is also possible in a corresponding national language. For this, a datum functioning as country setting 28 is analyzed in the memory of the type A medical device 10. The country setting 28 codes, for example, that all texts shall be outputted in the Greek language and correspondingly in the Greek alphabet by means of the display device 14 of the type A medical device 10. With regard to the display of pieces of information 20 for the type B medical device 12, it is then correspondingly checked whether the medical device database 26 comprises texts that can basically be displayed for the type B medical device 12 identified by the device identifier 24 and are available in the language coded by the country setting 28. If this is the case, the type A medical device 10 can assume a display of pieces of information 20 by means of its display device 14 for the type B medical device 12 and the initial suitability test, a form of a "pairing" (process of establishing connection for the first time) to some extent, is concluded. If successful, the type A medical device 10 transmits to the type B medical device 12 an acknowledgement message 30, which sends a signal to the type B medical device 12 that a display of its own pieces of information 20 by means of the display device 14 of the type A medical device 10 is possible. The type A medical device activates a guest display operation mode 40, in which the type A medical device 10 receives datagrams 22 from the type B medical device 12. The type B medical device 12 switches into a third-party display operation mode 42, in which the type B medical device 12 transmits a datagram 22 to the type A medical device 10 to display a respective piece of information 20.

The type B medical device 12 transmits a corresponding datagram 22 to the type A medical device 10 in case of a piece of information 20 to be displayed in the third-party display operation mode 42. This is shown in the view according to FIG. 3. For example, an alarm shall be displayed by means of the display device 14 of the type A medical device 10 as information 20 about an error situation that has occurred at the type B medical device 12. For this, the type B medical device 12 transmits a datagram 22 to the type A medical device 10. The datagram 22 comprises the device identifier 24 of the type B medical device 12 and an information identifier 44 in regard to the text to be displayed as information. On the part of the type A medical device 10, an access to the medical device database 26 is carried out with the received information identifier 44 and the country setting 28 and the result is the information 20 to be displayed in text form and in the language intended by the country setting 28, possibly in the language intended by the country setting 28 as well as in the alphabet likewise intended by the country setting 28.

Figure 3:
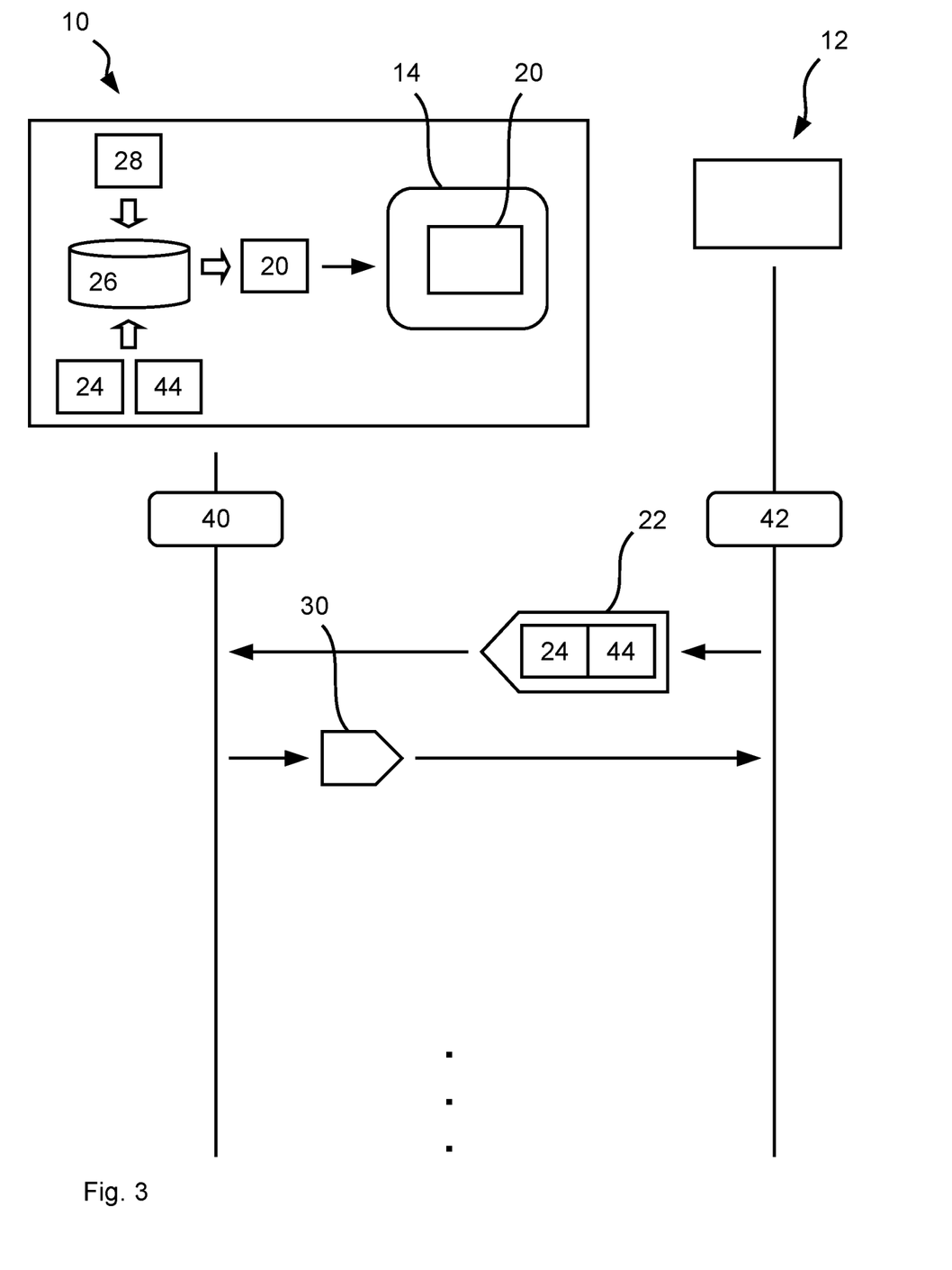
FIG. 3 is a schematic view illustrating a transmission of data between the two medical devices according to FIG. 1 for the purpose of the display of a piece of information for one of the two medical devices by the other medical device.

The medical device database 26 is organized in the simplest case, for example, in the form of at least one table with lines and columns. In the lines, each table comprises texts that can be outputted as information 20. In the columns, each table comprises the texts that can be outputted as information 20 in different languages and/or in different alphabets (different characters). Of course, an organization of each table with the different languages in individual lines and correspondingly the individual texts that can be outputted as information 20 in individual columns is likewise possible. Each table belongs to a type of medical device. Based on the device identifier 24 received together with the information identifier 44 by the type B medical device 12, a table of the medical device database 26 is accurately selected. A table position is accurately selected based on the information identifier 44 and the country setting 28, and the contents of this table position are the information 20 to be outputted. This information 20 is transmitted to the display device 14 and outputted there in a manner basically known per se.

The type A medical device optionally transmits an acknowledgement message 30 as confirmation to the type B medical device 12 to acknowledge the receipt of the datagram 22 with the information identifier 44 and/or to acknowledge the display of the information specified by means of the information identifier 44.

In the third-party operation mode 42, on the part of the type B medical device 12 with the sending of the datagram 22 with the information identifier 44 or with the receipt of an acknowledgement message 30 to the previously sent datagram 22, an activation of its own optical and/or acoustic signal element is suppressed. This guarantees that in case of an alarm situation, a signaling of the same alarm is not carried out both at the type B medical device 12 and at the type A medical device 10.

Optionally, a timer, which is stopped with the receipt of an acknowledgement message 30 to this datagram 22, is started with the transmitting of the datagram 22 with the information identifier 44. When the timer (watchdog) expires, i.e., if no acknowledgement message 30 is received within a time period predefined by the timer, the data transmission process on the part of the type B medical device 12 is interrupted and the third-party operation mode 42 is again deactivated because of the timer expiration. The type B medical device 12 then also signals the information to be outputted in an at least rudimentary manner and with its own means, for example, in the form of a display of the information identifier 44 by means of its own "simple" display element, be it optical (LED) or acoustic (horn, signal transmitter).

It is conceivable that a datagram 22 comprising the information identifier 44 does not comprise the device identifier 24. The datagram 22 comprises a transmitter identifier which corresponds to the protocol underlying the data transmission. This identifies the transmitting type B medical device 12. In case of the first data transmission (FIG. 2, pairing) from the type B medical device 12 to the type A medical device 10, the device identifier 24 and such a transmitter identifier are transmitted to the type A medical device 10. The type A medical device 10 can thus store the transmitter identifier of the type B medical device 12 and the device identifier 24 thereof in case of a successful pairing. In case of later datagrams 22 with an information identifier 44, the type A medical device 10 at first determines the device identifier 24 of the transmitting type B medical device 12 based on the transmitter identifier of this datagram 22 and then, as described above, the access to the medical device database 26 is carried out with this device identifier 24, which is then determined on the part of the type A medical device 10. This variant shall be seen below as an alternative and basically equivalent embodiment.

An exemplary, concrete embodiment of the guest display according to the view in FIG. 3 can be carried out corresponding to the steps explained below:

In a first step, the type B medical device 12, for example, a syringe pump, transmits a datagram 22 with an information identifier 44 to the type A medical device 10. Transmission of the datagram 22 takes place especially before or instead of an activation of an own optical and/or acoustic signal element, i.e., of a signal element of the type B medical device 12.

In a second step, the type A medical device 10 analyzes the information identifier 44 comprised by the datagram 22 received and carries out an access to the medical device database 26 with the information identifier 44, with the device identifier 24 also transmitted in the datagram 22 or determined on the part of the type A medical device 10 as well as with the country setting 28. The result of this access is the information 20 to be displayed in the corresponding national language, possibly in the corresponding national language and the corresponding alphabet. The determined information 20 is finally displayed by means of the display device 14 of the type A medical device 10.

In a basically optional third step, the type B medical device 12 activates its own "simple" display element and represents, for example, the information identifier 44 by means of this display element. This display is an additional display parallel to the display of the information 20 specified by the information identifier 44 by means of the display device 14 of the type A medical device 10.

A checking of a priority of the information identifier 44 received with the datagram 22 and/or of a device identifier 24 received with it is optionally carried out by the type A medical device 10 in the second step. The information identifier 44 specifies a piece of information 20 to be displayed. A piece of information 20 to be displayed may have a different relevance depending on its contents, so that a priority may be connected with each information identifier 44 and/or the resulting information 20. Such a priority linked with an information identifier 44 or with the resulting information 20 may be stored, for example, as a numerical value in the medical device database 26. Similarly, a priority may be connected with a device type of the type B medical device 12, i.e., the device identifier 24 identifying the device type, because, for example, a possible error message from a feeding pump is basically less critical than an error message from an infusion pump or the like. Such a priority linked with a device identifier 24 may also be stored in the medical device database 26, for example, likewise as a numerical value.

Depending on implementation, either the priority linked with the information identifier 44 or with the resulting information 20 or the priority linked with the device identifier 24 is analyzed in one and the same type A medical device 10 in case of a simultaneous or quasi simultaneous receipt of two datagrams 22, each with an information identifier 44. When different resulting priorities arise in relation to the two datagrams 22 received simultaneously or quasi simultaneously, the information 20, which traces back to a higher priority, is first displayed by means of the display device 14 of the type A medical device 10. The display of the other information 20 is deferred and takes place, for example, immediately after an acknowledgement of the information 20 displayed first at the type A medical device 10. In case of the priority-dependent display of a piece of information 20 for a remote type B medical device 12, priorities of the own display of the type A medical device 10 are basically also taken into consideration. A piece of information for a remote type B medical device 12 is then displayed, for example, only if no own display of the type A medical device 10 is necessary or if no higher-priority, own display of the type A medical device 10 is necessary.

In case of pieces of information 20 to be displayed simultaneously or overlapping over time for a remote type B medical device 12 or a plurality of remote type B medical devices 12, a display of the individual pieces of information 20 each following one another in succession can take place for a short and predefined time period (for example, 2-8 sec), in addition or as an alternative to taking priorities into consideration. It is likewise conceivable that a piece of information 20 or a plurality of pieces of information 20 are displayed semitransparently and translucently and are displayed each optionally without transparency briefly during a predefined or predefinable time period (for example, 2-8 sec) and in this case temporarily hide another piece of information 20 "lying under it" or an output of the type A medical device 10.

As information 20 to be displayed by means of the display device 14 of the type A medical device 10 for a remote type B medical device 12, operating instructions or a part of operating instructions of the respective type B medical device 12 basically also come into consideration. The operating instructions or a part of the operating instructions are then specified by means of the device identifier 24 and/or the information identifier 44. If the information identifier 44 codes, for example, an error situation or a special status of the type B medical device 12, which is explained in the operating instructions, the information identifier 44 specifies a concrete section of the operating instructions. Overall, the operating instructions of the type B medical device 12, a part of such operating instructions or a section of the operating instructions relevant in connection with an information identifier 44 can thus be displayed at the type A medical device 10 in the corresponding national language and in the corresponding alphabet, namely as a function of the country setting 28.

To this end, corresponding operating instructions are, of course, accessible for the type A medical device 10, for example, by these operating instructions being stored in the medical device database 26 in different languages as well as possibly in different alphabets (different characters). The access to the corresponding operating instructions then takes place according to the country setting 28, the device identifier 24 identifying the type B medical device 12 and possibly the information identifier 44. The above explanations for the receipt of the text form of a piece of information 20 from the medical device database 26 thus correspondingly apply to the receipt of the operating instructions, of a part of the operating instructions or of a concrete section of the operating instructions.

A "context-sensitive help" concerning the outputted information 20 in the form of a subsequent or simultaneous display of the operating instructions, of a part of the operating instructions or of a concrete section of the operating instructions can be offered to the user in case of outputting a piece of information belonging directly to the information identifier 44 especially in case of analysis of the information identifier 44 on the part of the type A medical device 10. The user thus receives, for example, pieces of information for eliminating the situation, on which the original transmission of the information identifier 44 to the type A medical device 10 is based. A concrete section of the operating instructions automatically identified because of the information identifier 44 can be displayed to the user, for example, in the form of a so-called "fault-cause-remedy table."

The hitherto described display of a piece of information 20 for a type B medical device 12 by means of a display device 14 of a type A medical device 10 that is communicatively connected to the type B medical device 12 can also be carried out by means of a mobile device, basically instead of a type A medical device 10 or in addition to a type A medical device 10, for example, by means of a smartphone, a handheld PC, a tablet PC, a laptop or the like. An initial pairing (FIG. 2) is at first also carried out with such a device, especially in order to ensure that the respective mobile device and the type B medical device 12 in a data network/network group are connected communicatively to one another and an assignment of the two devices in the data network is possible. The pairing is optionally repeated at regular intervals, for example, in a predefined or predefinable time grid, in order to ensure that the mobile device is still located in a reception area allowing the receipt of a datagram 22 from the type B medical device 12.

Even though the present invention was illustrated and described in more detail by the exemplary embodiment, the present invention is not limited by the example or examples disclosed and other variations may be derived herefrom by the person skilled in the art, without going beyond the scope of protection of the present invention.

Finally, individual aspects in the foreground of the description submitted here can be summarized briefly as follows: Proposed is a process for the operation of a type A medical device 10 together with at least one type B medical device 12, wherein the medical devices 10, 12 are connected communicatively to one another, wherein the type A medical device 10 comprises a display device 14 suitable for the display of texts, especially in different languages and/or different alphabets (different characters), and wherein the type B medical device 12 has no text display option of its own, wherein the type B medical device 12 transmits a datagram 22 with an information identifier 44 to the type A medical device 10 for displaying a textual or at least partially textual piece of information 20 and wherein upon receipt of an information identifier 44 from the medical device database 26, the type A medical device 10 loads a piece of information consistent with the information identifier 44 and displays this piece of information by means of its own display device 14 and for the type B medical device 12.

While specific embodiments of the invention have been shown and described in detail to illustrate the application of the principles of the invention, it will be understood that the invention may be embodied otherwise without departing from such principles.

LIST OF REFERENCE NUMBERS

10 Medical device, first medical device, type A medical device
12 Medical device, second medical device, type B medical device
14 Display device
16 Communication interface
18 Communication interface
20 Piece of information (to be displayed)
22 Datagram
24 Device identifier
26 Medical device database
28 Country setting
30 Acknowledgement message
40 Guest display operation mode
42 Third-party display operation mode
44 Information identifier

The invention claimed is:

1. A process for the operation of a first medical device together with at least one second medical device, the process comprising the steps of:
    connecting the first medical device together communicatively with the second medical device;
    providing the first medical device such that the first medical device comprises a display device configured to display texts in different languages and/or in different alphabets;
    providing the second medical device such that the second medical device has no text display device configured to display texts in different languages and/or in different alphabets;
    with the second medical device transmitting a datagram, with an information identifier, to the first medical device for displaying a textual information or displaying information that is at least partially textual;
    upon receipt of an information identifier from a medical device database, receiving information consistent with the information identifier from a database stored in a memory; and
    displaying said information consistent with the information identifier by the display device,
    wherein the first medical device takes into consideration a priority connected with the information in case of a display of information for the second medical device or a priority connected with the second medical device; and
    the priority arises on the basis of the piece of information, on the basis of the underlying information identifier, on the basis of the second medical device transmitting the information identifier and/or on the basis of a type of the second medical device transmitting the information identifier,
    wherein first information and second information with identical priorities are displayed in an alternating manner, at least partially overlapping one another and partially transparently and/or in non-overlapping areas of the display device of the first medical device.

2. A process in accordance with claim 1, wherein a language can be selected for the first medical device and an identifier of a selected language is stored in a country setting in memory; and
    upon receipt of the information identifier from the medical device database, the first medical device loads the information which is consistent with the information identifier and consistent with the country setting and displays the information by means of the display device.

3. A process in accordance with claim 1, wherein the datagram, transmitted to the first medical device from the second medical device, identifies the transmitting second medical device; and upon receipt of the information identifier, the first medical device loads information, which is consistent with the identification of the second medical device and with the information identifier or with the identification of the second medical device, with the information identifier and with the country setting.

4. A process in accordance with claim 1, wherein a language can be selected for the first medical device and an identifier of the selected language is stored in a country setting in memory;
the datagram transmitted from the second medical device to the first medical device identifies the transmitting second medical device; and
based on the identification of the second medical device and based on the country setting, operating instructions for the second medical device are loaded from the medical device database and from another database available for the first medical device and are displayed as information by means of the display device of the first medical device.

5. A process in accordance with claim 4, wherein with additional consideration of the information identifier, a concrete section of the operating instructions for the second medical device is loaded and displayed by the display device.

6. A process according to claim 1, wherein a control program in the form of a computer program with program code executes the process steps on the first medical device.

7. A process according to claim 1, wherein a program in the form of a computer program with program code executes the process steps on the second medical device.

8. A medical device to be connected communicatively with a second medical device, the first medical device comprising:
a display device configured to display texts in different languages and/or in different alphabets, wherein the second medical device has no text display configured to display texts in different languages and/or in different alphabets and the second medical device is configured to transmit a datagram, with an information identifier, to the first medical device for displaying a textual information or displaying information that is at least partially textual on the display device; and
a processing unit with a memory, the processing unit being configured to receive the datagram from the second medical device and, based on the information identifier to obtain information consistent with the information identifier from a medical device database, wherein the processing unit loads the information consistent with the information identifier for display of said information consistent with the information identifier by the display device,
wherein the first medical device takes into consideration a priority connected with the information in case of a display of information for the second medical device or a priority connected with the second medical device; and
the priority arises on the basis of the piece of information, on the basis of the underlying information identifier, on the basis of the second medical device transmitting the information identifier and/or on the basis of a type of the second medical device transmitting the information identifier,
wherein first information and second information with identical priorities are displayed in an alternating manner, at least partially overlapping one another and partially transparently and/or in non-overlapping areas of the display device of the first medical device.

9. A medical device to act as a second medical device to be connected communicatively with a first medical device, the second medical device comprising:
a processing unit with a memory, wherein the second medical device does not comprise a display device that is suitable for a display of texts in different languages and/or in different alphabets, wherein the processing unit is configured to connect communicatively with the first medical device that comprises a display device configured to display texts in different languages and/or in different alphabets, transmit a datagram, with an information identifier, to the first medical device for displaying a textual information or displaying information that is at least partially textual to load information consistent with the information identifier at the first medical device upon receipt of an information identifier from a medical device database and displaying said information consistent with the information identifier by the display device at the first medical device,
wherein the first medical device takes into consideration a priority connected with the information in case of a display of information for the second medical device or a priority connected with the second medical device; and
the priority arises on the basis of the piece of information, on the basis of the underlying information identifier, on the basis of the second medical device transmitting the information identifier and/or on the basis of a type of the second medical device transmitting the information identifier,
wherein first information and second information with identical priorities are displayed in an alternating manner, at least partially overlapping one another and partially transparently and/or in non-overlapping areas of the display device of the first medical device.

10. A medical device system comprising:
a first medical device comprising:
a display device configured to display texts in different languages and/or in different alphabets; and
a processing unit with a memory, the processing unit being configured to receive a datagram, with an information identifier and based on a medical device database, to load information consistent with the information identifier and generate a display of said information consistent with the information identifier by the display device; and
a second medical device comprising a processing unit and a memory, wherein the second medical device does not comprise a display device that is suitable for a display of texts at least in different languages and/or in different alphabets, wherein the processing unit of the second medical device is configured to connect communicatively with the first medical device and to transmit the datagram, with the information identifier, to the first medical device for displaying a textual information or displaying information that is at least partially textual to load information consistent with the information identifier at the first medical device upon receipt of the information identifier from the medical device database and displaying said information consistent with the information identifier by the display device at the first medical device,
wherein the first medical device takes into consideration a priority connected with the information in case of a display of information for the second medical device or a priority connected with the second medical device; and the priority arises on the basis of the piece of information, on the basis of the underlying information identifier, on the basis of the second medical device transmitting the information identifier and/or on the basis of a type of the second medical device transmitting the information identifier, wherein first information and second information with identical priorities are displayed in an alternating manner, at least partially overlapping one another and partially transparently and/or in non-overlapping areas of the display device of the first medical device.

* * * * *